(12) United States Patent
Buttar

(10) Patent No.: US 10,893,865 B2
(45) Date of Patent: Jan. 19, 2021

(54) MAGNETIC WOUND CLOSURE SYSTEMS

(71) Applicant: MAYO FOUNDATION FOR MEDICAL EDUCATION AND RESEARCH, Rochester, MN (US)

(72) Inventor: Navtej S. Buttar, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 230 days.

(21) Appl. No.: 15/565,513

(22) PCT Filed: Apr. 8, 2016

(86) PCT No.: PCT/US2016/026696
§ 371 (c)(1),
(2) Date: Oct. 10, 2017

(87) PCT Pub. No.: WO2016/168081
PCT Pub. Date: Oct. 20, 2016

(65) Prior Publication Data
US 2018/0078257 A1    Mar. 22, 2018

Related U.S. Application Data

(60) Provisional application No. 62/146,764, filed on Apr. 13, 2015.

(51) Int. Cl.
*A61B 17/08* (2006.01)
*A61M 37/00* (2006.01)
(Continued)

(52) U.S. Cl.
CPC ........ *A61B 17/08* (2013.01); *A61B 17/00234* (2013.01); *A61B 17/122* (2013.01);
(Continued)

(58) Field of Classification Search
CPC ............... A41F 1/002; A61M 37/0015; A61M 2037/0023; A61M 2037/0061;
(Continued)

(56) References Cited

U.S. PATENT DOCUMENTS 3,825,010 A    7/1974 McDonald
6,398,713 B1 *  6/2002 Ewing .................... A61N 2/008
                                                   600/9
(Continued)

FOREIGN PATENT DOCUMENTS

CN    203953717    11/2014
DE    2447681      4/1974

OTHER PUBLICATIONS

Macmillan dictionary, Definition of "sprocket", 2015, https://www.macmillandictionary.com/dictionary/american/sprocket (Year: 2015).*
(Continued)

*Primary Examiner* — Todd J Scherbel
*Assistant Examiner* — Mikail A Mannan
(74) *Attorney, Agent, or Firm* — Fish & Richardson P.C.

(57) ABSTRACT

Devices, systems, and methods can be used for the closure of surgical wounds. For example, surgical wounds can be closed using magnetic closure devices rather than the conventional methods of using sutures, clips, or staples. Additionally, in some implementations the magnetic closure devices provided herein are delivered laparoscopically or endoscopically via a vacuum catheter.

7 Claims, 4 Drawing Sheets

(51) Int. Cl.
 *A61B 17/00* (2006.01)
 *A61B 17/122* (2006.01)
 *A61M 5/142* (2006.01)
 *A61B 17/10* (2006.01)
 *A61B 17/128* (2006.01)

(52) U.S. Cl.
 CPC ......... *A61M 37/0015* (2013.01); *A61B 17/10* (2013.01); *A61B 17/1285* (2013.01); *A61B 2017/0034* (2013.01); *A61B 2017/00561* (2013.01); *A61B 2017/00818* (2013.01); *A61B 2017/00876* (2013.01); *A61B 2017/00893* (2013.01); *A61B 2017/081* (2013.01); *A61M 5/142* (2013.01); *A61M 5/14244* (2013.01); *A61M 2037/0023* (2013.01); *A61M 2037/0061* (2013.01)

(58) Field of Classification Search
 CPC ....... A61B 17/10; A61B 17/08; A61B 17/122; A61B 2017/00876; A61B 2017/081
 See application file for complete search history.

(56) References Cited

U.S. PATENT DOCUMENTS

| | | | |
|---|---|---|---|
| 6,611,707 B1* | 8/2003 | Prausnitz | A61B 5/14514 604/21 |
| 2006/0241691 A1 | 10/2006 | Wilk | |
| 2008/0262543 A1 | 10/2008 | Bangera et al. | |
| 2012/0123387 A1 | 5/2012 | Gonzalez et al. | |
| 2013/0325046 A1 | 12/2013 | Terwiske et al. | |
| 2014/0214078 A1 | 7/2014 | Moustafa | |
| 2015/0047105 A1* | 2/2015 | Fonzo | A41F 1/002 2/265 |
| 2015/0088195 A1* | 3/2015 | Moustafa | A61B 17/085 606/216 |
| 2017/0065803 A1* | 3/2017 | Birchall | A61M 37/0015 |

OTHER PUBLICATIONS

PCT International Search Report and Written Opinion in Interntaional Appln. No. PCT/US2016/26696, dated Jul. 12, 2016, 8 pages.
PCT International Preliminary Report on Patentability in Interntaional Appln. No. PCT/US2016/26696, dated Oct. 17, 2017, 8 pages.

* cited by examiner

MAGNETIC WOUND CLOSURE SYSTEMS

CROSS REFERENCE TO RELATED APPLICATIONS

This application is a National Stage application under 35 U.S.C. § 371 of International Application No. PCT/US2016/026696, having an International Filing Date of Apr. 8, 2016, which claims the benefit of U.S. Provisional Application No. 62/146,764, filed Apr. 13, 2015. The disclosure of the prior applications are considered part of and are incorporated by reference in the disclosure of this application.

BACKGROUND

1. Technical Field

This document relates to devices, systems, and methods for the closure of wounds. For example, this document relates to devices, systems, and methods for closing wounds such as surgical incisions, post-polypectomy wounds, as well as a preventive measure before polyp resection using magnetic closure devices rather than the conventional methods of using sutures, clips, or staples.

2. Background Information

An incision is a cut through the skin or mucosa that is made during surgery or endoscopy. It is also called a surgical or endoscopic wound. Some wounds are small, and others are long. Safely and effectively closing tissue these wounds is a challenge in the surgical, laparoscopic, and endoscopic fields.

Wound closure techniques have evolved from early developments in suturing materials to advanced techniques such as synthetic sutures, absorbable sutures, staples, tapes, and adhesive compounds. Some of the main aims of skin or mucosal closure are good tissue approximation, ease of performance, pain control, good patient acceptability, minimal scarring, and acceptable cosmetic appearance (particularly of skin wounds).

The need to remove lesions from the wall of the colon is common and growing worldwide. The likelihood of having polyps increases with age. Approximately half of the people over the age of 60 have at least one polyp and often more. Polyps are considered pre-cancerous, which means that while they are not cancer, if left untreated they may develop into cancer. Colon lesions are typically found during colon cancer screening tests, such as a colonoscopy or flexible sigmoidoscopy. Lesions of the colon can be in the form of polyps that protrude from the colon lining with a mushroom-like shape, or flat lesions that are flush on the colon wall.

Benign and early malignant lesions of the colon can usually be removed endoscopically using an electrocautery snare, hot snare, cold snare, or electrocautery knife devices. A saline-assisted polypectomy procedure is often used for the removal of large flat colon lesions. The procedure starts with injection of a solution into the submucosal space under the lesion, creating a safety cushion. The cushion lifts the lesion to facilitate its removal and minimizes mechanical or electrocautery damage to the deep layers of the GI tract wall.

When lesions become still larger and invasively encompass more than just the mucosal layers of the colon, a colectomy procedure is often performed whereby the full thickness of the colon wall tissue is removed along with the lesion. This procedure is typically performed using open surgery techniques.

SUMMARY

This document provides devices, systems, and methods for the closure of wounds. For example, this document provides devices, systems, and methods for closing wounds such as surgical incisions using magnetic closure devices instead of the conventional methods of using sutures, clips, or staples. Devices and methods are provided for both external skin wound closure, as well as internal wound closure (e.g., from a polypectomy in a colon, etc.). Additionally, in some implementations the magnetic closure devices provided herein are delivered laparoscopically or endoscopically via a vacuum catheter that can be used to controllably navigate and deploy the magnetic closure devices.

In one implementation, a wound closure system includes a first wound closure device and a second wound closure device. The first wound closure device includes a first casing that defines a first tunnel and a first manifold; a first flexible magnet strip that is slidably engageable within the first tunnel; and a plurality of first wound approximator micro-needles extending from the first casing and in fluid communication with the first manifold. The second wound closure device includes a second casing that defines a second tunnel and a second manifold; a second flexible magnet strip that is slidably engageable within the second tunnel; and a plurality of second wound approximator micro-needles extending from the second casing and in fluid communication with the second manifold. The first flexible magnet strip is selectively magnetically coupleable with the second flexible magnet strip such that, when the first flexible magnet strip is engaged within the first tunnel and the second flexible magnet strip is engaged within the second tunnel, the first casing and the second casing are selectively magnetically coupleable to each other.

Such a wound closure system may optionally include one or more of the following features. At least some of the first wound approximator micro-needles or the second wound approximator micro-needles may be hypodermic needles through which a fluidic medication can flow when the fluid medication is pressurized within the first manifold or second manifold. At least some of the first wound approximator micro-needles or the second wound approximator micro-needles may be C-shaped. The wound closure may further comprise a fluidic medication pump in fluid communication with at least one of the first manifold and the second manifold. The first flexible magnet strip may be selectively magnetically coupleable with the second flexible magnet strip by positionally adjusting relative polarities of magnets on the first flexible magnet strip or the second flexible magnet strip.

In another implementation, a method of closing a wound in tissue includes installing a first wound closure device on a first side of the wound and installing a second wound closure device on a second side of the wound opposite of the first side of the wound. The first wound closure device includes a first casing that defines a first tunnel and a first manifold; a first flexible magnet strip that is slidably engageable within the first tunnel; and a plurality of first wound approximator micro-needles extending from the first casing and in fluid communication with the first manifold. The second wound closure device includes a second casing that defines a second tunnel and a second manifold; a second flexible magnet strip that is slidably engageable within the second tunnel; and a plurality of second wound approximator micro-needles extending from the second casing and in fluid communication with the second manifold. The first flexible magnet strip is selectively magnetically coupleable with the second flexible magnet strip such that, when the first flexible magnet strip is engaged within the first tunnel and the second flexible magnet strip is engaged within the second tunnel, the first casing and the second casing are selectively magnetically coupleable to each other. The method further includes magnetically coupling the first flexible magnet strip with the second flexible magnet strip such that the first casing becomes generally abutted to the second casing, and such that the plurality of first wound approximator micro-needles and the plurality of second wound approximator micro-needles draw the wound closed.

Such a method of closing a wound in tissue may optionally include one or more of the following features. The method may further comprise, after magnetically coupling the first flexible magnet strip with the second flexible magnet strip, administering a fluid medication through at least some of the plurality of first wound approximator micro-needles and the plurality of second wound approximator micro-needles. The magnetically coupling of the first flexible magnet strip with the second flexible magnet strip may comprise positionally adjusting relative polarities of magnets on the first flexible magnet strip or the second flexible magnet strip.

In another implementation, a wound closure system includes a first wound closure device, a second wound closure device, and a delivery catheter. The first wound closure device includes a first casing that defines a first tunnel; a first flexible magnet strip that is slidably engageable within the first tunnel; and a plurality of first tethering spikes extending from the first casing. The second wound closure device includes a second casing that defines a second tunnel; a second flexible magnet strip that is slidably engageable within the second tunnel; and a plurality of second tethering spikes extending from the second casing. The first flexible magnet strip is selectively magnetically coupleable with the second flexible magnet strip such that, when the first flexible magnet strip is engaged within the first tunnel and the second flexible magnet strip is engaged within the second tunnel, the first casing and the second casing are selectively magnetically coupleable to each other. The delivery catheter is configured for deploying the first wound closure device or the second wound closure device. In some embodiments, the delivery catheter is a vacuum catheter.

Such a wound closure system may optionally include one or more of the following features. The wound closure system may further comprise an endoscope defining a first working channel that is configured to slidably receive the delivery catheter. The delivery catheter may be a first delivery catheter configured for deploying the first wound closure device, and the wound closure system may further comprise a second delivery catheter configured for deploying the second wound closure device. The endoscope may define a second working channel that is configured to slidably receive the second delivery catheter.

In another implementation, a method of resecting a portion of an intestinal wall includes deploying, at a first target site on the intestinal wall, a first wound closure device; deploying, at a second target site on the intestinal wall adjacent to the first target site, a second wound closure device; magnetically coupling the first flexible magnet strip with the second flexible magnet strip such that the first casing becomes magnetically to the second casing; and resecting a portion of the intestinal wall after magnetically coupling the first flexible magnet strip with the second flexible magnet strip such that the clamped two layers of the intestinal wall close the intestinal wall at the resected portion. The first wound closure device includes a first casing that defines a first tunnel; a first flexible magnet strip that is slidably engageable within the first tunnel; and a plurality of first tethering spikes extending from the first casing. The second wound closure device includes a second casing that defines a second tunnel; a second flexible magnet strip that is slidably engageable within the second tunnel; and a plurality of second tethering spikes extending from the second casing. The first flexible magnet strip is selectively magnetically coupleable with the second flexible magnet strip such that, when the first flexible magnet strip is engaged within the first tunnel and the second flexible magnet strip is engaged within the second tunnel, the first casing and the second casing are selectively magnetically coupleable to each other. The magnetically coupling results in clamping two layers of the intestinal wall between the first casing and the second casing.

Such a method of resecting a portion of an intestinal wall may optionally include one or more of the following features. The intestinal wall may be a colon wall. The polyp may be resected along with the portion of the colon wall. The first flexible magnet strip may be selectively magnetically coupleable with the second flexible magnet strip by positionally adjusting relative polarities of magnets on the first flexible magnet strip or the second flexible magnet strip. The deploying steps may be performed using one or more vacuum catheters.

Particular embodiments of the subject matter described in this document can be implemented to realize one or more of the following advantages. First, in some embodiments the wound closure devices provided herein are quick and convenient to install. For example, using the devices and techniques provided herein, in many cases no suturing or stapling of the wound is required. Rather, in some embodiments magnetic attraction between two or more wound closure device portions is used to facilitate wound closure. Further, the wound closure devices are easy to remove in case of infection, and for other reasons.

Second, in some embodiments the wound closure devices provided herein are selectively closeable and openable. In some such embodiments, a magnetic closure means is used. In some embodiments, by adjusting the relative polarity alignment of the magnets, the wound closure devices can be selectively coupled and decoupled from each other. When the wound closure devices are coupled, wound closure forces are applied and wound healing can take place. Conversely, when the wound closure devices are decoupled, wound closure forces are released from the tissue surrounding the wound.

Third, in some embodiments the wound closure devices provided herein include a means of administering pain control drugs. The devices and techniques provided herein thereby enhance patient comfort and wound healing.

Fourth, in some embodiments the wound closure devices provided herein can be delivered laparoscopically and/or endoscopically. In some implementations the magnetic closure devices provided herein are delivered laparoscopically or endoscopically via a vacuum catheter that can be used to controllably navigate and deploy the magnetic closure devices. As such, patients can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices, systems, and methods for the closure of wounds. For example, this document provides devices, systems, and methods for closing wounds such as surgical incisions using magnetic closure devices instead of the conventional methods of using sutures, clips, or staples.

The devices, systems, and methods provided herein can also be used to treat other types of wounds such as, but not limited to, accidental lacerations, stab wounds, burst aneurysms, amputations, and the like. The devices, systems, and methods provided herein can be used to close wounds that are internal or external, linear or curved, and planar or non-planar. The devices, systems, and methods provided herein are applicable to humans and to non-human animals.

Figure 2:
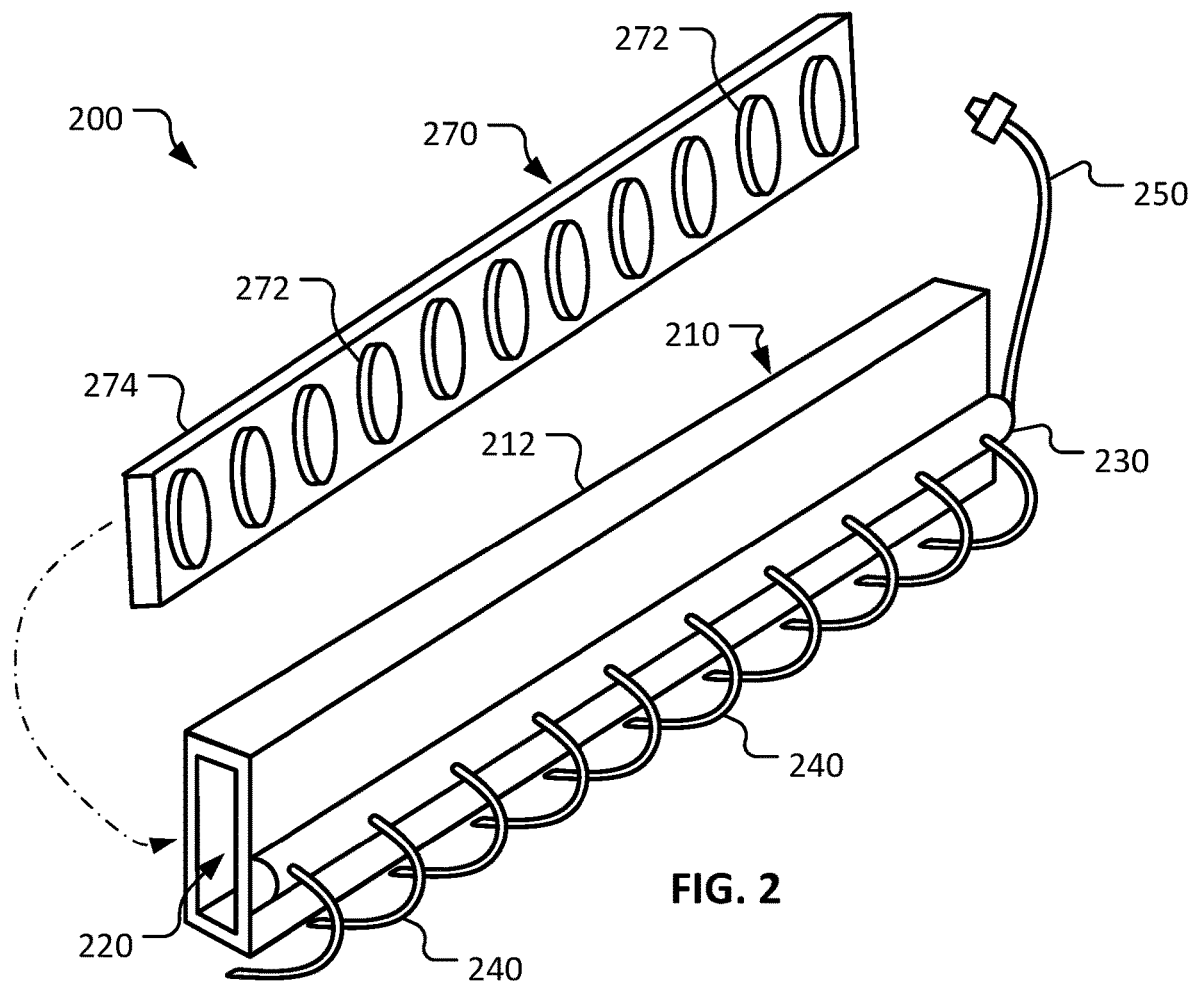
FIG. 2 is an exploded perspective view of a portion of an example wound closure device in accordance with some embodiments provided herein.
Figure 3:
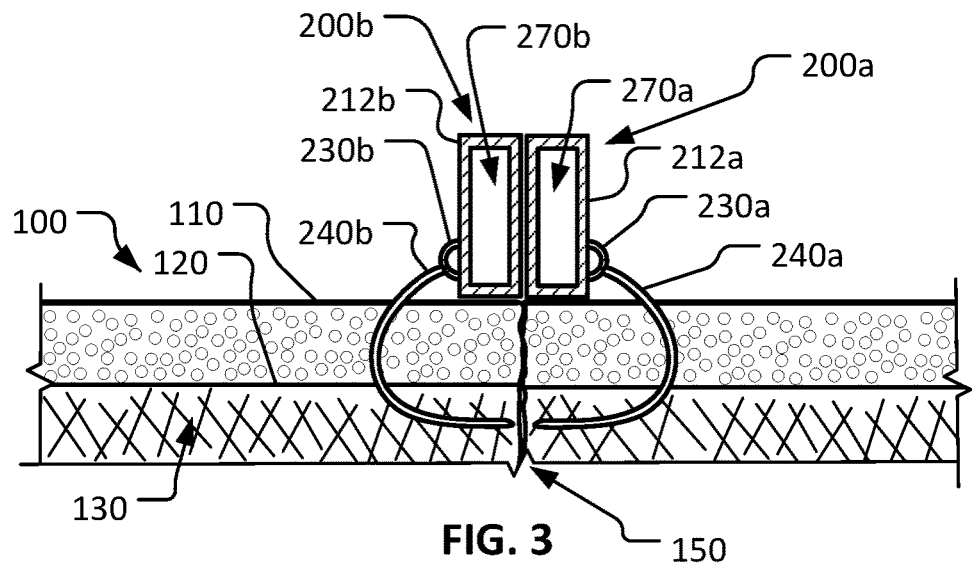
FIG. 3 is a sectional view showing two wound closure device portions of FIG. 2 in a coupled configuration to thereby apply closure forces for tissue approximation of the wound of FIG. 1, in accordance with some embodiments provided herein.
Figure 4:
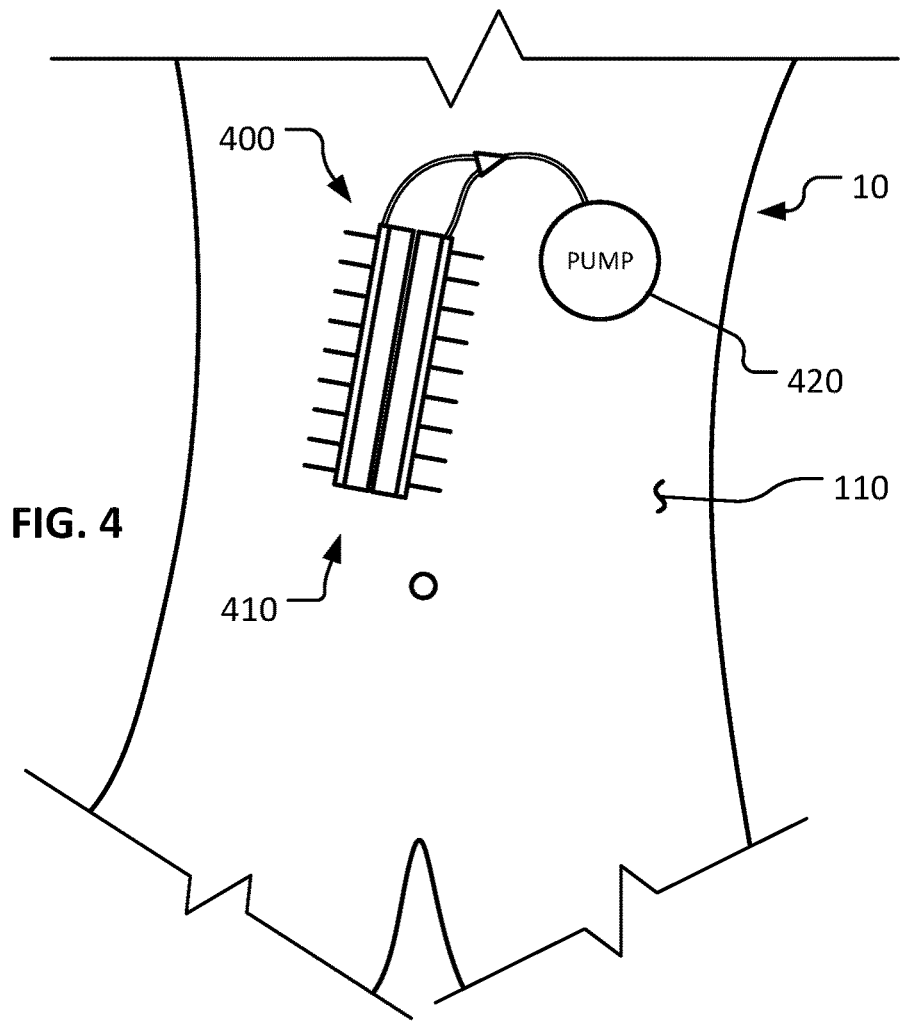
FIG. 4 shows a schematic view of a patient's abdomen with an example wound closure device and drug pump being used to close a wound in accordance with some embodiments.
Figure 7:
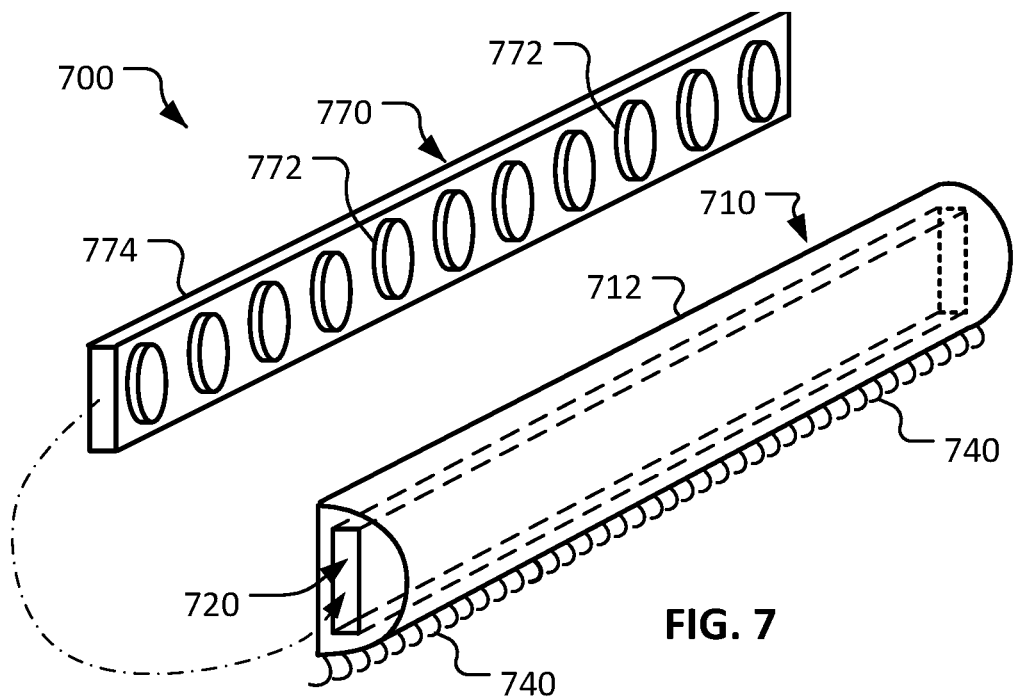
FIG. 7 is an exploded perspective view of a portion of another example wound closure device in accordance with some embodiments provided herein.
Figure 8:
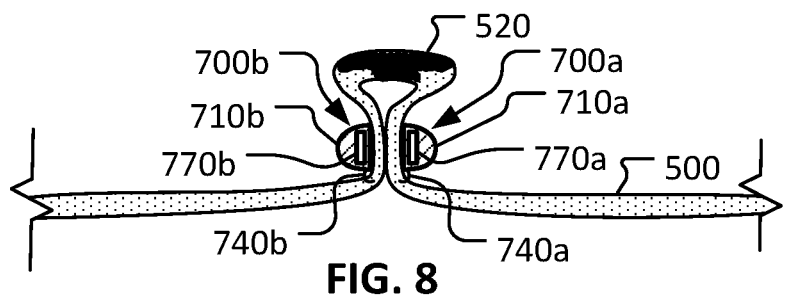
FIG. 8 is a sectional view showing two wound closure device portions of FIG. 7 in a coupled configuration to thereby apply closure forces in preparation for resection of the tethered polyp of FIG. 5, in accordance with some embodiments provided herein.
Figure 9:
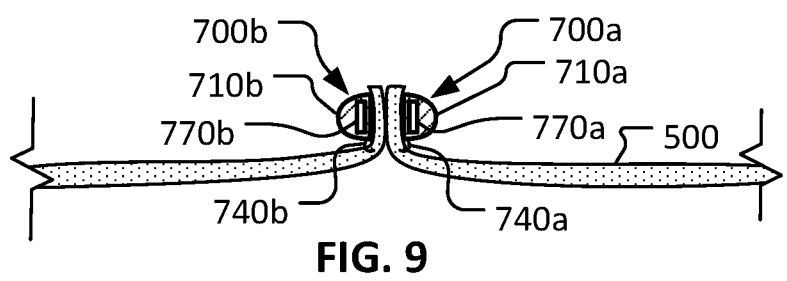
FIG. 9 is a sectional view showing the two wound closure device portions of FIG. 8 applying wound closure forces to the intestinal wall after resection of the tethered polyp.

It should be understood that two types of wound closure devices, systems, and methods are provided herein. A first type of wound closure device is intended for use primarily on the exterior of the body. This example wound closure device, and the method of use thereof, is depicted in FIGS. 2-4. A second type of wound closure device is intended for use primarily in the interior of the body. This example wound closure device, and the method of use thereof, is depicted in FIGS. 7-9.

Figure 1:
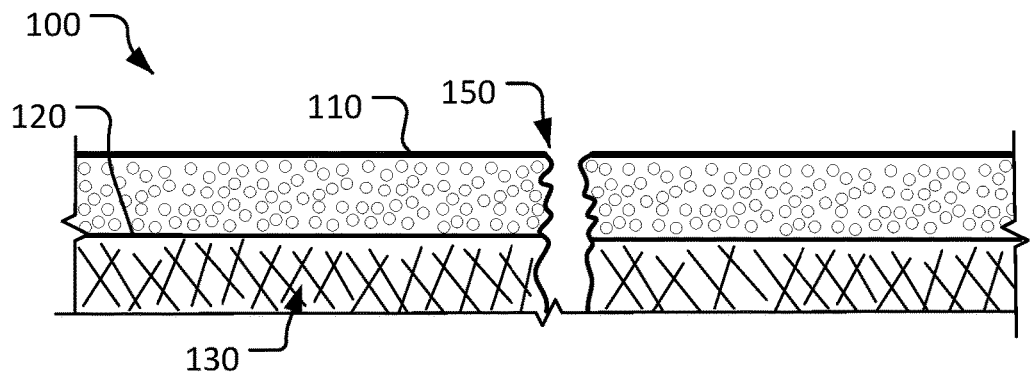
FIG. 1 is a sectional view of a wound, including illustrations of the skin, fascia, and muscle tissues surrounding the wound.

With reference to FIG. 1, a sectional view of an example wound 150 can be used to illustrate the method of using the wound closure devices provided herein. In this example, wound 150 penetrates through a patient's skin 110, fascia 120, and into muscle tissues 130. In this example, wound 150 is a surgical wound, but it should be understood that the wound closure devices described herein can be used for other types of wounds in addition to surgical wounds.

With reference to FIG. 2, an example wound closure device 200 broadly includes a wound closure sheath 210 and a flexible magnet strip 270. One or more flexible magnet strips 270 can be selectively engaged with wound closure sheath 210. In this example, flexible magnet strip 270 can be inserted (e.g., slid) into a tunnel 220 of wound closure sheath 210. Alternatively, or additionally, other coupling techniques can be used to selectively engage one or more flexible magnet strips 270 with wound closure sheath 210.

Wound closure sheath 210 includes a casing 212 that defines tunnel 220. Attached to casing 212 is a medication carrying lumen or manifold 230 from which a plurality of wound approximator micro-needles 240 extend. A medication supply line 250 is fluidly connected to medication carrying manifold 230. Fluidic medications can flow through medication supply line 250, into medication carrying manifold 230, and then into the plurality of wound approximator micro-needles 240. As one example, in some implementations, pain medications such as lidocaine hydrochloride can be delivered via the wound approximator micro-needles 240 (e.g., syringes).

In some embodiments, casing 212 is made of metallic materials such as stainless steel, aluminum, and alloys thereof. In some embodiments, casing 212 is made of polymeric materials such as polycarbonate, nylon, and the like. In some embodiments, casing 212 is made of a combination of metallic and polymeric materials. In some embodiments, casing 212 is made from manufacturing techniques such as extrusion, molding, machining, overmolding, using adhesives, welding, and the like, and combinations thereof.

In particular embodiments, casing 212 is flexible such that it can be contoured to a desired configuration (e.g., to comply with a curved wound). In some embodiments, casing 212 is malleable.

In some embodiments, the size of wound approximator micro-needles 240 are about 28 gauge needles. In some embodiments, the size of wound approximator micro-needles 240 are in a range of about 26 gauge to about 30 gauge. In some embodiments, the size of wound approximator micro-needles 240 are in a range of about 24 gauge to about 32 gauge.

In the depicted embodiment, wound approximator micro-needles 240 have a generally c-shape. In some embodiments, wound approximator micro-needles 240 have other shapes such as, but not limited to, L-shaped, linear, v-shaped, U-shaped, and the like. In some embodiments, such as the depicted embodiment, each of the wound approximator micro-needles 240 is the same shape. Alternatively, in some embodiments one or more wound approximator micro-needles 240 is shaped differently that one or more other wound approximator micro-needles 240.

Example wound closure device 200 also includes flexible magnet strip 270. Flexible magnet strip 270 includes one or more magnets 272 and a substrate 274. In some embodiments, substrate 274 is flexible and/or malleable. In various embodiments, magnets 272 are movable in relation to substrate 274. As described further below, movability of magnets 272 in relation to substrate 274 can facilitate selective coupling between two wound closure devices 200 by adjusting the relative polarity alignment of the magnets 272 between the two wound closure devices 200. For example, in some embodiments magnets 272 can pivot, spin, flip, translate, and/or combinations thereof so as to move in relation to substrate 274.

In some embodiments, magnets 272 are neodymium magnets. In some embodiments, magnets 272 are other types of magnets including, but not limited to, electromagnets.

With reference to FIG. 3, a first wound closure sheath 210a is coupled with a second wound closure sheath 210b so as to approximate and close wound 150. It can be envisioned that flexible magnet strip 270a is magnetically coupled with flexible magnet strip 270b. In this operative configuration, wound approximator micro-needles 240a and wound approximator micro-needles 240b are both in position to delivery medication to muscle tissues 130 proximate to wound 150 via manifolds 230a and 230b respectively.

To install first wound closure sheath 210a, a healthcare professional can penetrate wound approximator micro-needles 240a through skin 110 using an arc motion path, so that wound approximator micro-needles 240a penetrate down to muscle tissues 130. The installation of second wound closure sheath 210b can be performed in the same fashion on the opposite side of wound 150.

In some implementations, flexible magnet strips 270a and/or 270b are already installed within tunnels 220 (refer to FIG. 2) prior to penetration of skin 110. Thereafter, flexible magnet strips 270a and/or 270b can be positionally adjusted so that the polarities of the magnets in flexible magnet strips 270a and 270b align (e.g., north poles to south poles) to cause a magnetic attraction therebetween. In some implementations, one or both of flexible magnet strips 270a and/or 270b become installed within tunnels 220 after penetration of skin 110.

To remove first wound closure sheath 210a and/or second wound closure sheath 210b from wound 150, the reverse of the installation procedure described above can be performed. For example, flexible magnet strips 270a and/or 270b can be made to decouple from each other. This can be accomplished, for example, by positionally adjusting the magnets so that the polarities of the magnets in flexible magnet strips 270a and 270b align (e.g., north to north poles, and south to south poles) to release magnetic attraction therebetween. Thereafter, first wound closure sheath 210a and second wound closure sheath 210b can be removed such that wound approximator micro-needles 240a and 240b are removed from engagement with the patient.

With reference to FIG. 4, a patient 10 can be treated using an example wound closure system 400. Wound closure system 400 includes two or more wound closure devices 410 in a coupled arrangement (as described above) and a medication pump 420. In the depicted embodiment, medication pump 420 is a wearable pump. In some embodiments, medication pump 420 is a remote pump such as a bedside pump, pole-mounted pump, and the like.

While the depicted implementation shows two wound closure devices 410 in a coupled arrangement, it should be understood that in some implementations four, six, eight, or more than eight wound closure devices 410 in a coupled arrangement are used in a particular implementation (to close a particular wound). While the depicted implementation shows the closure of a generally linear wound using two generally linear wound closure devices 410, it should be understood that curved wounds can be closed using the devices provided herein. For example, in some embodiments curved wounds can be closed by using flexible/malleable wound closure devices 410 that are configured into curves, and/or by using multiple wound closure devices 410 that are installed at non-zero angles in relation to each other along the curved wound. In some such embodiments, adjacent wound closure devices 410 (on the same side of a wound) interlock with each other.

Figure 5:
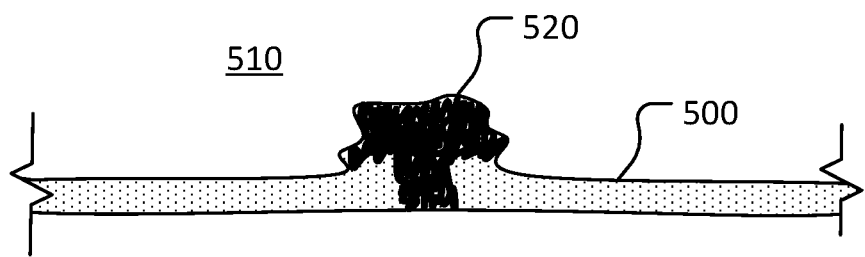
FIG. 5 shows a sectional view of an intestinal wall in which a tethered polyp is present.

With reference to FIG. 5, a polyp 520 in an intestinal wall 500 can be treated using some embodiments of the wound closure devices provided herein. This is an example of a submucosa invasion of polyp 520, such that polyp 520 extends into the intestinal lumen 510 and is tethered to the full thickness of intestinal wall 500 tissue. In this example, resection of intestinal wall 500 tissue is needed to remove polyp 520.

Figure 6:
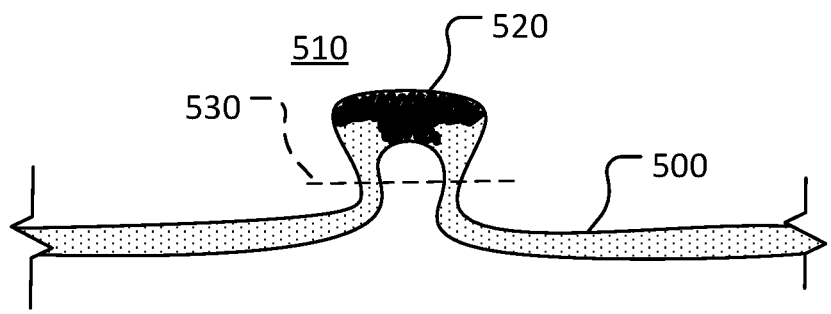
FIG. 6 depicted a sectional view of the tethered polyp of FIG. 5 after an injection of saline to lift the tethered polyp in accordance with some implementations.

With reference to FIG. 6, polyp 520 and a portion of intestinal wall 500 has been raised into the intestinal lumen 510. This raising is performed in preparation for resection of polyp 520. In some implementations, a saline injection is used to raise polyp 520. In some implementations, other means are used to raise polyp 520. It can be envisioned that cutting along line 530 will resect polyp 520 and the portion of intestinal wall 500 to which polyp 520 is tethered. However, such a cut would also result in a perforation and/or of intestinal wall 500.

With reference to FIG. 7, an example wound closure device 700 broadly includes a wound closure sheath 710 and a flexible magnet strip 770. One or more flexible magnet strips 770 can be selectively engaged with wound closure sheath 710. In this example, flexible magnet strip 770 can be inserted (slid) into a tunnel 720 of wound closure sheath 710. Alternatively, or additionally, other coupling techniques can be used to selectively engage one or more flexible magnet strips 770 with wound closure sheath 710.

In some embodiments, wound closure device 700 can be deployed using a catheter device through a working channel of a scope. As such, resection and wound closure of intestinal walls (and other internal tissues) can be achieved using minimally invasive techniques. In some such embodiments, a vacuum catheter is used to deploy wound closure device 700 to a target location internal to a patient. In some implementations, the vacuum catheter can be used to controllably navigate and deploy the magnetic closure devices to the target location(s).

In the depicted embodiment, wound closure device 700 includes a plurality of tethering spikes 730. Tethering spikes 730 are very small needles that penetrate tissue to latch wound closure device 700 to the tissue.

Flexible magnet strip 770 can be constructed of any of the materials and using any of the techniques described above in reference to flexible magnet strip 270. Wound closure sheath 710 can be constructed of any of the materials and using any of the techniques described above in reference to wound closure sheath 210.

With reference to FIG. 8, a first wound closure device 700a is coupled with a second wound closure device 700b with two layers of intestinal wall 500 therebetween. It can be envisioned that a first flexible magnet strip 770a is magnetically coupled with a second flexible magnet strip 770b.

In this operative configuration, tethering spikes 730a and 730b are both in engagement with intestinal wall 500. It should be understood that multiple first wound closure devices 700a and multiple second wound closure devices 700b may be installed in a particular target location (e.g., to provide closure of a relatively longer wound).

To install first wound closure device 700a, a healthcare professional can use a deployment catheter (e.g., vacuum catheter in some embodiments) and scope (e.g., laparoscope or endoscope) to implant first wound closure sheath 710a such that tethering spikes 730a are in engagement with intestinal wall 500. The installation of second wound closure device 700b can be performed in the same fashion on the opposite side of lifted polyp 520. In some implementations, a double-channel scope is used, and first wound closure device 700a and second wound closure device 700b are deployed via separate channels.

In some implementations, flexible magnet strips 770a and/or 770b are already installed within tunnels 720 (refer to FIG. 7) prior to deployment. Thereafter, flexible magnet strips 770a and/or 770b can be positionally adjusted so that the polarities of the magnets in flexible magnet strips 770a and 770b align (e.g., north poles to south poles) to cause a magnetic attraction therebetween. In some implementations, one or both of flexible magnet strips 770a and/or 770b become installed within tunnels 720 after deployment. In some embodiments, the deployment catheter can be used to positionally adjust the polarities of the magnets in flexible magnet strips 770a and 770b.

With reference also to FIG. 9, resection of polyp 520 and a portion of intestinal wall 500 has taken place. First wound closure device 700a is coupled second wound closure device 700b, with two layers of intestinal wall 500 therebetween, to close the wound resulting from the resection. After a period of time, the two layers of intestinal wall 500 will tend to grow together and heal. After at that time, first wound closure device 700a and second wound closure device 700b may detach from intestinal wall 500 and be naturally expelled from the patient's body.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A wound closure system comprising:
    a first wound closure device comprising:
        a first casing that defines a first tunnel, the first casing having a first front face surface;
        a first manifold attached on a side of the first casing opposite of the first front face;
        a first flexible magnet strip that is selectively engageable with the first casing by user insertion of the first flexible magnet strip into the first tunnel; and
        a plurality of first C-shaped wound approximator micro-needles extending from the first manifold and in fluid communication with the first manifold; and
    a second wound closure device comprising:
        a second casing that defines a second tunnel, the second casing having a second front face surface;
        a second manifold attached on a side of the second casing opposite of the second front face;
        a second flexible magnet strip that is selectively engageable with the second casing by user insertion of the second flexible magnet strip into the second tunnel; and
        a plurality of second C-shaped wound approximator micro-needles extending from the second manifold and in fluid communication with the second manifold,
    wherein the first flexible magnet strip is selectively magnetically coupleable with the second flexible magnet strip such that, when the first flexible magnet strip is engaged within the first tunnel and the second flexible magnet strip is engaged within the second tunnel, the first front face surface and the second front face surface are selectively magnetically coupleable to abut against each other, and
    wherein, while the first front face surface and the second front face surface are abutted against each other: (i) the plurality of first C-shaped wound approximator micro-needles directionally extend from the first manifold laterally away from the second casing and then turn toward the second casing and (ii) the plurality of second C-shaped wound approximator micro-needles directionally extend from the second manifold laterally away from the first casing and then turn toward the first casing.

2. The wound closure system of claim 1, wherein at least some of the first C-shaped wound approximator micro-needles or the second C-shaped wound approximator micro-needles are hypodermic needles through which a fluidic medication can flow when the fluid medication is pressurized within the first manifold or second manifold.

3. The wound closure system of claim 1, further comprising a fluidic medication pump in fluid communication with at least one of the first manifold and the second manifold.

4. The wound closure system of claim 1, wherein the first flexible magnet strip is selectively magnetically coupleable with the second flexible magnet strip by positionally adjusting relative polarities of magnets on the first flexible magnet strip or the second flexible magnet strip.

5. A method of closing a wound in tissue, the method comprising:
   installing a first wound closure device on a first side of the wound, wherein the first wound closure device comprises:
      a first casing that defines a first tunnel, the first casing having a first front face surface;
      a first manifold attached on a side of the first casing opposite of the first front face;
      a first flexible magnet strip that is selectively engageable with the first casing by user insertion of the first flexible magnet strip into the first tunnel; and
      a plurality of first C-shaped wound approximator micro-needles extending from the first manifold and in fluid communication with the first manifold;
   installing a second wound closure device on a second side of the wound opposite of the first side of the wound, wherein the second wound closure device comprises:
      a second casing that defines a second tunnel, the second casing having a second front face surface;
      a second manifold attached on a side of the second casing opposite of the second front face;
      a second flexible magnet strip that is selectively engageable with the second casing by use insertion of the second flexible magnet strip into the second tunnel; and
      a plurality of second C-shaped wound approximator micro-needles extending from the second manifold and in fluid communication with the second manifold,
   wherein the first flexible magnet strip is selectively magnetically coupleable with the second flexible magnet strip such that, when the first flexible magnet strip is engaged within the first tunnel and the second flexible magnet strip is engaged within the second tunnel, the first front face surface and the second front face surface are selectively magnetically coupleable to abut against each other; and
   magnetically coupling the first flexible magnet strip with the second flexible magnet strip such that the first front face surface becomes generally abutted against the second front face surface, and
   wherein, while the first front face surface and the second front face surface are abutted against each other: (i) the plurality of first C-shaped wound approximator micro-needles directionally extend from the first manifold laterally away from the second casing and then turn toward the second casing and (ii) the plurality of second C-shaped wound approximator micro-needles directionally extend from the second manifold laterally away from the first casing and then turn toward the first casing, such that the plurality of first C-shaped wound approximator micro-needles and the plurality of second C-shaped wound approximator micro-needles draw the wound closed.

6. The method of claim 5, further comprising, after magnetically coupling the first flexible magnet strip with the second flexible magnet strip, administering a fluid medication through at least some of the plurality of first C-shaped wound approximator micro-needles and the plurality of second C-shaped wound approximator micro-needles.

7. The method of claim 5, wherein the magnetically coupling of the first flexible magnet strip with the second flexible magnet strip comprises positionally adjusting relative polarities of magnets on the first flexible magnet strip or the second flexible magnet strip.

* * * * *